United States Patent
Dai et al.

(10) Patent No.: US 11,814,465 B2
(45) Date of Patent: Nov. 14, 2023

(54) ORGANIC-INORGANIC HYBRID MATERIAL, FABRICATION PROCESS OF THE SAME AND ITS STARTING MATERIAL

(71) Applicant: CHANDA CHEMICAL CORP., Taipei (TW)

(72) Inventors: Sheng-hong A. Dai, Taipei (TW); Chien-Hsin Wu, Taipei (TW); Ying-Chi Huang, Taipei (TW); Yu-Hsiang Huang, Taipei (TW); Shih-Chieh Yeh, Taipei (TW); Ru-Jong Jeng, Taipei (TW); Jau-Hsiang Yang, Taipei (TW)

(73) Assignee: CHANDA CHEMICAL CORP., Taipei (TW)

( * ) Notice: Subject to any disclaimer, the term of this patent is extended or adjusted under 35 U.S.C. 154(b) by 0 days.

(21) Appl. No.: 17/893,643

(22) Filed: Aug. 23, 2022

(65) Prior Publication Data
US 2023/0002537 A1    Jan. 5, 2023

Related U.S. Application Data

(60) Division of application No. 16/704,445, filed on Dec. 5, 2019, now Pat. No. 11,453,738, which is a continuation of application No. PCT/CN2019/104479, filed on Sep. 5, 2019.

(51) Int. Cl.
| | |
|---|---|
| *C08K 9/06* | (2006.01) |
| *C08L 63/00* | (2006.01) |
| *C08L 75/04* | (2006.01) |
| *C08L 79/08* | (2006.01) |
| *C08G 18/10* | (2006.01) |
| *C08G 18/32* | (2006.01) |
| *C08G 18/71* | (2006.01) |
| *C08G 18/44* | (2006.01) |
| *C08K 3/30* | (2006.01) |
| *C08K 9/04* | (2006.01) |
| *C08K 3/22* | (2006.01) |
| *C07C 263/04* | (2006.01) |
| *C07C 263/00* | (2006.01) |
| *C09D 175/04* | (2006.01) |
| *C09D 179/08* | (2006.01) |
| *C23C 18/12* | (2006.01) |

(52) U.S. Cl.
CPC .......... *C08G 18/10* (2013.01); *C07C 263/00* (2013.01); *C07C 263/04* (2013.01); *C08G 18/3215* (2013.01); *C08G 18/44* (2013.01); *C08G 18/718* (2013.01); *C08K 3/22* (2013.01); *C08K 3/30* (2013.01); *C08K 9/04* (2013.01); *C08K 2003/3009* (2013.01); *C08K 2201/003* (2013.01); *C23C 18/1254* (2013.01)

(58) Field of Classification Search
CPC .. C09D 163/00; C09D 175/04; C09D 179/08; C08L 63/00; C08L 75/04; C08L 79/08; C08K 9/06
USPC ................................ 523/427; 528/85, 350
See application file for complete search history.

(56) References Cited

U.S. PATENT DOCUMENTS 6,319,311 B1 * 11/2001 Katz ................... C08G 18/289
428/447

* cited by examiner

*Primary Examiner* — Michael J Feely
(74) *Attorney, Agent, or Firm* — WPAT, PC

(57) ABSTRACT

An organic-inorganic hybrid material is disclosure. The organic-inorganic hybrid material contains 5~50 wt % of inorganic compounds and has a characteristic peak at 1050±50 cm$^{-1}$ in FTIR spectrum. Furthermore, the invention also provides a fabricating process of the organic-inorganic hybrid material as well as its starting material "isocyanates". In particular, the isocyanates are prepared from carbonate containing compounds and amines.

15 Claims, 6 Drawing Sheets

ORGANIC-INORGANIC HYBRID MATERIAL, FABRICATION PROCESS OF THE SAME AND ITS STARTING MATERIAL

CROSS-REFERENCE TO RELATED APPLICATION

This is a divisional application of U.S. patent application Ser. No. 16/704,445 filed Dec. 5, 2019, which is incorporated by reference herein in its entirety.

TECHNICAL FIELD OF THE INVENTION

The present invention relates to an organic-inorganic hybrid material and its fabricating process as well as its starting material "isocyanates". In particular, the organic-inorganic hybrid material contains 5~50 wt % of inorganic compounds and has a characteristic peak at $1050 \pm 50$ cm$^{-1}$ in FTIR spectrum.

BACKGROUND OF THE INVENTION

Composite materials, such as organic-inorganic hybrid materials and thermoset composites, are widely applied in the optical, electronic, medical device areas. The success of composites takes advantages from the fillers such as the inorganic particles or nature fibers with long or short length, and versatile polymers to tailored made properties required and required applications. However, these applications are usually hinged by the incompatibility between organic and inorganic materials since the phase separation caused by poor compatibility between fillers and polymers.

Based on the aforementioned description, an organic-inorganic hybrid material and its fabricating process by using a novel additive are required for developing.

SUMMARY OF THE INVENTION

In one aspect, the present invention provides an organic-inorganic hybrid material. The organic-inorganic hybrid material comprises a product produced from a sol-gel reaction of a composition, wherein the product comprises 5-50 wt % of inorganic compounds based on total weight of the product, and a structure of the organic-inorganic hybrid material has a characteristic peak at $1050 \pm 50$ cm$^{-1}$ in FTIR spectrum.

In one aspect, the composition comprises a prepolymer and one selected from the group consisting of a compound having a formula (1), a product prepared from an isocyanate and a phenolic compound, diphenyl carbonate and an inorganic bead.

In one aspect, the prepolymer comprises a polyurethane prepolymer, an epoxy oligomer or a polyamic acid. Preferably, the prepolymer has molecular weight between 5,000 and 50,000 Da.

In one aspect, the compound having a formula (1) is a modifier and its function is to enhance compatibility of organic materials and inorganic materials.

The compound having a formula (1) is shown as following structure.

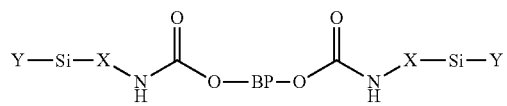
(1)

BP represents a polyphenol or a halogenated polyphenol; and X is ($-CH_2-$)$_m$, or O and m is a integer of 1 to 10. Y is (H)$_a$, ($-OH$)$_b$, ($-OCH_3$)$_c$, ($-OCH_2CH_3$)$_d$ or ($-OCH_2CH_2CH_3$)$_e$ and the sum of a, b, c, d and e is equal to 3. a, b, c, d, ore is a number of 0 to 3.

In one aspect, the phenolic compound comprises 2,2-bis (4-hydroxyphenyl) propane (bisphenol A), 2,2-bis(4-hydroxyphenyl) methane (bisphenol F), a compound having a formula (2), a compound having a formula (3) or a compound having a formula (4).

The compound having a formula (2) is shown as following structure.

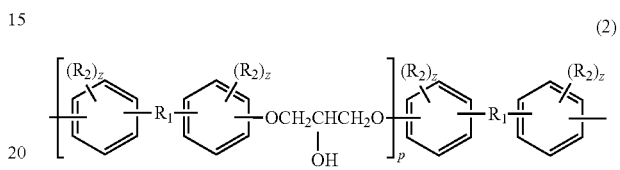
(2)

The compound having a formula (3) is shown as following structure.

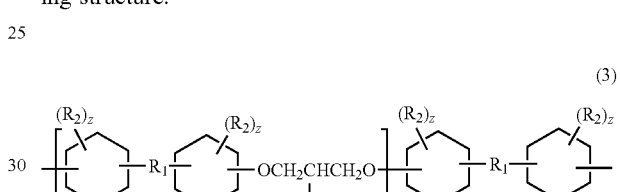
(3)

The compound having a formula (4) is shown as following structure.

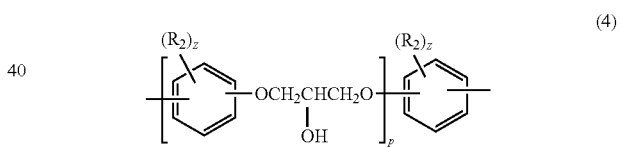
(4)

$R_1$ independently represents a alkyl group with carbon numbers$\leq$10, a cycloalkyl group, a halogen substituted alkyl group, a carbonyl group, a sulfonyl group, a sulfinyl group or a polyphenolic group.

$R_2$ independently represents H, a alkyl group with carbon numbers$\leq$5, a cycloalkyl group, a halogen substituted alkyl group, a carbonyl group, a sulfonyl group, a sulfinyl group or a polyphenolic group.

Z is an integer of 1~4; and p$\leq$20.

In conclusion, the organic-inorganic hybrid material is prepared from four different formulations via the sol-gel reaction, respectively. The first formulation comprises the compound having a formula (1) and the prepolymer. The second formulation comprises the product prepared from the isocyanates and phenolic compound and the prepolymer. The third formulation comprises diphenyl carbonate and the prepolymer, and the fourth formulation comprises the inorganic bead and the prepolymer.

In another aspect, the present invention discloses a process of preparation of the organic-inorganic hybrid material. The invented process is able to use waste polycarbonate as a starting material and carbon dioxide is not release in the invented process. Accordingly, the invented process fixes carbon dioxide in the structure of the organic-inorganic hybrid material, and prolongs carbon cycles. In brief, the invented process is an environmental-friendly process.

Typically, the process comprises following steps.

(I) Provides a compound having a formula (1), or a product prepared from a isocyanate and a phenolic compound, or diphenyl carbonate or a inorganic bead; (II) add the compound having a formula (1), or the product prepared from the isocyanate and the phenolic compound, or diphenyl carbonate or the inorganic bead to a prepolymer having molecular weight between 5,000 and 50,000 Da to form a mixture, wherein the mixture comprising 10-60 wt % of the prepolymer based on total weight of the mixture; and (III) perform a sol-gel process to proceed the mixture of an organic-inorganic hybrid material by hydrolysis and condensation reaction, wherein the organic-inorganic hybrid material comprises 5-50 wt % of inorganic compounds based on its total weight, and structure of the organic-inorganic hybrid material has a characteristic peak at $1050 \pm 50$ cm$^{-1}$ in FTIR spectrum.

Generally, a solvent is required for making the mixture to form a homogeneous phase. The solvent comprises tetrahydrofuran, dimethyl sulfoxide, dimethylformamide, N-methyl-2-pyrrolidone or anisole.

The hydrolysis and condensation reaction is a hydrolytic condensation and performed at 20-60° C.

In still another aspect, the present invention provides a method of preparation of isocyanates from carbonate containing compounds.

The method of preparation of isocyanates from carbonate containing compounds is a non-phosgene route. In particular, the method involves two heating stages for producing isocyanates. Carbon dioxide is not release from the heating stages. Furthermore, one of the carbonate containing compounds is waste polycarbonates, so the method can solve pollution problem caused by waste polymers.

The method of preparation of isocyanates from carbonate containing compounds comprises following steps.

Provide a mixture comprises a carbonate containing compound, an aliphatic amine or amino silane and a solvent, wherein the carbonate containing compound comprises polycarbonate, diphenyl carbonate or its mixture, and perform a converting process to have the carbonate containing compound react with the aliphatic amine or amino silane to produce isocyanates.

The converting process comprises a first heating stage and a second heating stage, wherein the first heating stage operates at temperature between 40 and 150° C., and the second heating stage operates at temperature between 100 and 250° C. under vacuum.

The vacuum pressure is 0.0001-400 mmHg.

Typically, concentration of the carbonate containing compound based on total weight of the mixture is 5-50 wt %.

According to the aforementioned invention content, the invented organic-inorganic hybrid material is produced from the composition comprises the modifier. The modifier significantly improves or increases the compatibility of the organic material and inorganic material, so as to enhance properties and/or performance of the invented organic-inorganic hybrid material, such as waterproof and film formation. Secondly, the process of preparation of the invented organic-inorganic hybrid material is able to solve pollution problem because a waste polymer, such as waste polycarbonate, is use as one of the starting materials in the process. Moreover, the invention provides a method for preparing isocyanates via a non-phosgene route. Carbon dioxide is not release from the method. Hence, the method effectively prolongs carbon dioxide in carbon cycle.

BRIEF DESCRIPTION OF THE PREFERRED EMBODIMENTS

Figure 1:
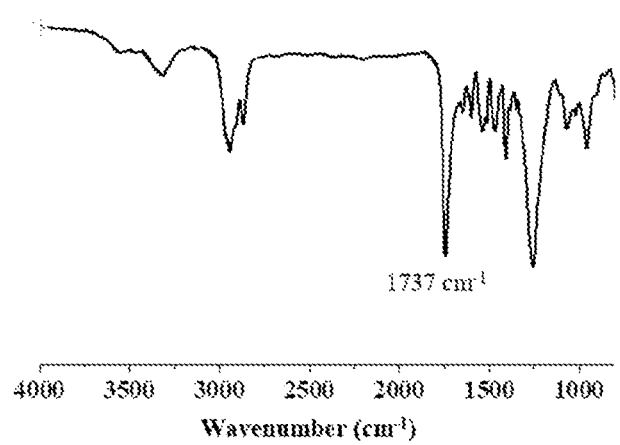
FIG. 1 is a FTIR spectrum directed to the product prepared in experiment No. 1.

In the first embodiment, the present invention discloses an organic-inorganic hybrid material. The organic-inorganic hybrid material comprises a product produced from a sol-gel reaction of a composition, wherein the product comprises 5-50 wt % of inorganic compounds based on total weight of the product, and structure of the organic-inorganic hybrid material has a characteristic peak at $1050 \pm 50$ cm$^{-1}$ in FTIR spectrum.

The composition comprises a prepolymer and one selected from the group consisting of a compound having a formula (1), a product prepared from an isocyanate and a phenolic compound, diphenyl carbonate and an inorganic bead.

In one example of the first embodiment, the prepolymer comprises a polyurethane prepolymer, an epoxy oligomer or a polyamic acid. The polyamic acid is a precursor of polyimide.

In one example of the first embodiment, the prepolymer has molecular weight between 5,000 and 50,000 Da.

In one example of the first embodiment, the compound having a formula (1) is shown as following structure.

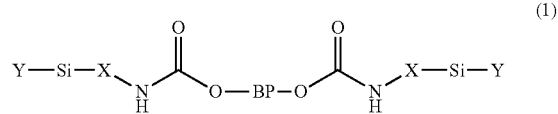

BP represents a polyphenol or a halogenated polyphenol; and X is ($-CH_2-)_m$, or O and m is a integer of 1 to 10. Y is $(H)_a$, $(-OH)_b$, $(-OCH_3)_c$, $(-OCH_2CH_3)_d$ or $(-OCH_2CH_2CH_3)_e$ and the sum of a, b, c, d and e is equal to 3. a, b, c, d, ore is a number of 0 to 3.

The compound having a formula (1) is a modifier and its function is to enhance compatibility of organic materials and inorganic materials.

In an representative example of the first embodiment, the compound having a formula (1) is (4-(2-(4-hydroxyphenyl)propan-2-yl)phenyl(3-(trimethoxy silyl)prop yl)carbamate.

In one example of the first embodiment, the isocyanate comprises hexyl isocyanate, octyl isocyanate, dodecyl isocyanate, octadecyl isocyanate, cyclohexyl isocyanate, trimethylsilyl isocyanate, 3-(triethoxysilyl)propyl isocyanate, 3-(trimethoxysilyl)propyl isocyanate, phenylethyl isocyanate, methyl isocyanate, ethyl isocyanate, propyl isocyanate, eicosyl isocyanate or tetracosyl isocyanate.

In one example of the first embodiment, the phenolic compound comprises 2,2-bis(4-hydroxyphenyl) propane (bisphenol A), 2,2-bis(4-hydroxyphenyl) methane (bisphenol F), a compound having a formula (2), a compound having a formula (3) or a compound having a formula (4).

The compound having a formula (2) is shown as following structure.

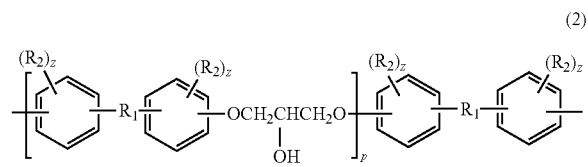

The compound having a formula (3) is shown as following structure.

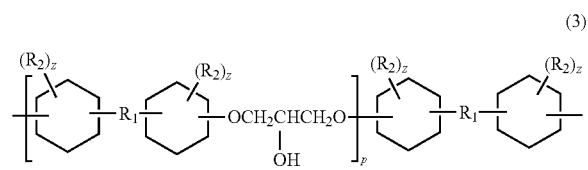

The compound having a formula (4) is shown as following structure.

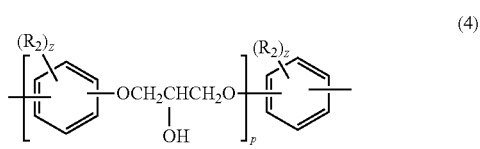

$R_1$ independently represents a alkyl group with carbon numbers≤10, a cycloalkyl group, a halogen substituted alkyl group, a carbonyl group, a sulfonyl group, a sulfinyl group or a polyphenolic group.

$R_2$ independently represents H, a alkyl group with carbon numbers≤5, a cycloalkyl group, a halogen substituted alkyl group, a carbonyl group, a sulfonyl group, a sulfinyl group or a polyphenolic group.

Z is an integer of 1~4; and p≤20.

In one example of the first embodiment, the inorganic bead is produced by coating the compound having a formula (1), or the product prepared from the isocyanate and the phenolic compound onto a surface of an inorganic particle.

In one example of the first embodiment, the inorganic particle comprises silicon oxide, silicon sulfide, aluminum oxide, aluminum sulfide, titanium oxide, titanium sulfide, germanium oxide, germanium sulfide, iron oxide, iron sulfide, barium oxide, barium sulfide, zinc oxide, zinc sulfide, copper oxide, copper sulfide, chromium oxide, chromium sulfide, niobium oxide, niobium sulfide, manganese oxide, manganese sulfide, tin oxide, tin sulfide, lithium oxide, lithium sulfide, cerium oxide, cerium sulfide, cobalt oxide, cobalt sulfide, SiO2, TiO2, ZnO, $ZrO_2$, $Fe_2O_3$, $BaTiO_3$, $LiNbO_3$, CdSe, CuO, $BaZrO_3$, $Cr_2O_3$, $Nb_2O_5$, $CsO_2$, $FeTiO_3$, FeS, mixture of $Al_2O_3$ and $TiO_2$, mixture of $Al_2O_3$ and $ZrO_2$, $MnO_2$, SnO or ZnS.

In one example of the first embodiment, the inorganic particle has average diameters between 20 to 1,000 nm.

In one example of the first embodiment, the inorganic compounds are prepared by hydrolysis and condensation reaction. The hydrolysis and condensation reaction is hydrolytic condensation.

In one example of the first embodiment, the inorganic compounds comprise silicon oxide, silicon sulfide, aluminum oxide, aluminum sulfide, titanium oxide, titanium sulfide, germanium oxide, germanium sulfide, iron oxide, iron sulfide, barium oxide, barium sulfide, zinc oxide, zinc sulfide, copper oxide, copper sulfide, chromium oxide, chromium sulfide, niobium oxide, niobium sulfide, manganese oxide, manganese sulfide, tin oxide, tin sulfide, lithium oxide, lithium sulfide, cerium oxide, cerium sulfide, cobalt oxide, cobalt sulfide, SiO2, TiO2, ZnO, $ZrO_2$, $Fe_2O_3$, $BaTiO_3$, $LiNbO_3$, CdSe, CuO, $BaZrO_3$, $Cr_2O_3$, $Nb_2O_5$, $CsO_2$, $FeTiO_3$, FeS, mixture of $Al_2O_3$ and $TiO_2$, mixture of $Al_2O_3$ and $ZrO_2$, $MnO_2$, SnO or ZnS.

In the second embodiment, the invention discloses a process of preparation of the organic-inorganic hybrid material described in the first embodiment.

The process comprises following steps: (I)Provides a compound having a formula (1), or a product prepared from a isocyanate and a phenolic compound, or diphenyl carbonate or a inorganic bead; (II)add the compound having a formula (1), or the product prepared from the isocyanate and the phenolic compound, or diphenyl carbonate or the inorganic bead to a prepolymer having molecular weight between 5,000 and 50,000 Da to form a mixture, wherein the mixture comprising 10-60 wt % of the prepolymer based on total weight of the mixture; and (III) perform a sol-gel process to proceed the mixture of an organic-inorganic hybrid material by hydrolysis and condensation reaction, wherein the organic-inorganic hybrid material comprises 5-50 wt % of inorganic compounds based on its total weight, and structure of the organic-inorganic hybrid material has a characteristic peak at 1050±50 $cm^{-1}$ in FTIR spectrum.

In one example of the second embodiment, the compound having a formula (1) is shown as following structure.

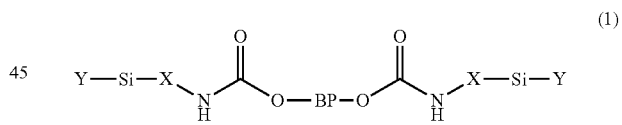

BP represents a polyphenol or a halogenated polyphenol; and X is $(-CH_2-)_m$, or O and m is a integer of 1 to 10. Y is $(H)_a$, $(-OH)_b$, $(-OCH_3)_c$, $(-OCH_2CH_3)_d$ or $(-OCH_2CH_2CH_3)_e$ and the sum of a, b, c, d and e is equal to 3. a, b, c, d, or e is a number of 0 to 3.

The compound having a formula (1) is a modifier and its function is to enhance compatibility of organic materials and inorganic materials.

In an representative example of the second embodiment, the compound having a formula (1) is (4-(2-(4-hydroxyphenyl)propan-2-yl)phenyl(3-(trimethoxysilyl)propyl)carbamate.

In one example of the second embodiment, the isocyanate comprises hexyl isocyanate, octyl isocyanate, dodecyl isocyanate, octadecyl isocyanate, cyclohexyl isocyanate, trimethylsilyl isocyanate, 3-(triethoxysilyl)propyl isocyanate, 3-(trimethoxysilyl)propyl isocyanate, phenylethyl isocyanate, methyl isocyanate, ethyl isocyanate, propyl isocyanate, eicosyl isocyanate or tetracosyl isocyanate.

In one example of the second embodiment, the phenolic compound comprises 2,2-bis(4-hydroxyphenyl) propane (bisphenol A), 2,2-bis(4-hydroxyphenyl) methane (bisphenol F), a compound having a formula (2), a compound having a formula (3) or a compound having a formula (4).

The compound having a formula (2) is shown as following structure.

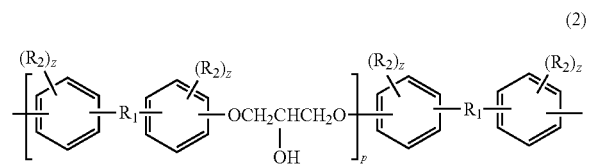

(2)

The compound having a formula (3) is shown as following structure.

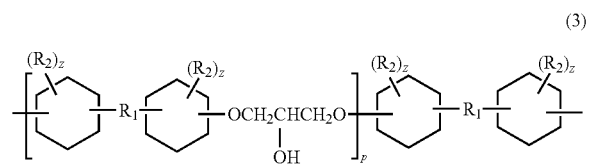

(3)

The compound having a formula (4) is shown as following structure.

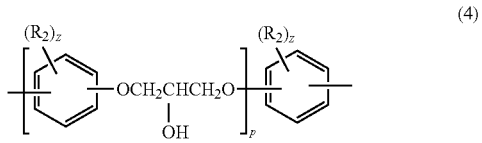

(4)

$R_1$ independently represents a alkyl group with carbon numbers≤10, a cycloalkyl group, a halogen substituted alkyl group, a carbonyl group, a sulfonyl group, a sulfinyl group or a polyphenolic group.

$R_2$ independently represents H, a alkyl group with carbon numbers≤5, a cycloalkyl group, a halogen substituted alkyl group, a carbonyl group, a sulfonyl group, a sulfinyl group or a polyphenolic group.

Z is an integer of 1-4; and p≤20.

In one example of the second embodiment, the inorganic bead is produced by coating the compound having a formula (1), or the product prepared from the isocyanate and the phenolic compound onto a surface of an inorganic particle.

In one example of the second embodiment, the inorganic particle comprises silicon oxide, silicon sulfide, aluminum oxide, aluminum sulfide, titanium oxide, titanium sulfide, germanium oxide, germanium sulfide, iron oxide, iron sulfide, barium oxide, barium sulfide, zinc oxide, zinc sulfide, copper oxide, copper sulfide, chromium oxide, chromium sulfide, niobium oxide, niobium sulfide, manganese oxide, manganese sulfide, tin oxide, tin sulfide, lithium oxide, lithium sulfide, cerium oxide, cerium sulfide, cobalt oxide, cobalt sulfide, $SiO2$, $TiO_2$, $ZnO$, $ZrO_2$, $Fe_2O_3$, $BaTiO_3$, $LiNbO_3$, $CdSe$, $CuO$, $BaZrO_3$, $Cr_2O_3$, $Nb_2O_5$, $CsO_2$, $FeTiO_3$, $FeS$, mixture of $Al_2O_3$ and $TiO_2$, mixture of $Al_2O_3$ and $ZrO_2$, $MnO_2$, $SnO$ or $ZnS$.

In one example of the second embodiment, the inorganic particle has average diameters between 20 to 1,000 nm.

In one example of the second embodiment, the prepolymer comprises a polyurethane prepolymer, an epoxy oligomer or a polyamic acid.

In one example of the second embodiment, the mixture further comprises a solvent, an additive or its combination. Preferably, the solvent comprises tetrahydrofuran, dimethyl sulfoxide, dimethylformamide, N-methyl-2-pyrrolidone or anisole.

In one example of the second embodiment, the additive comprises boric acid, phosphoric acid, hydrochloride acid, sulfuric acid, nitric acid, acetic acid, formic acid, propionic acid, alkali metal hydroxide, sodium phosphate, aliphatic amine, piperidine and its derivatives, imidazole and its derivatives or nitrogen heterocyclic compounds.

In one example of the second embodiment, the hydrolysis and condensation reaction is performed at a temperature between 20 and 60° C.

In a third embodiment, the invention provides a method for preparation of isocyanates from carbonate containing compounds.

The method comprises following steps: provide a mixture comprises a carbonate containing compound, an aliphatic amine or amino silane and a solvent, wherein the carbonate containing compound comprises polycarbonate, diphenyl carbonate or its mixture; and perform a converting process to have the carbonate containing compound react with the aliphatic amine or amino silane to produce isocyanates.

In one example of the third embodiment, the converting process comprises a first heating stage and a second heating stage, wherein the first heating stage operates at temperature between 40 and 150° C., and the second heating stage operates at temperature between 100 and 250° C. under vacuum. Preferably, the vacuum pressure is 0.0001-400 mmHg In one example of the third embodiment, the aliphatic amine comprises benzylamine, ethylamine, phenethylamine, propylamine, 3-phenylpropylamine, butylamine, 4-phenylbutylamine, pentylamine, 5-phenylpentylamine, hexylamine, 6-phenylhexylamine, isobutylamine, aminoethylpiperazine, 1-methylpiperazine, 3-morpholinopropylamine or aminoethylpiperazine.

In one example of the third embodiment, the amino silane comprises (3-aminopropyl)triethoxysilane or (3-aminopropyl)trimethoxysilane.

In one example of the third embodiment, the mixture comprises 5-50 wt % of the carbonate containing compound based on total weight of the mixture.

In one example of the third embodiment, the solvent comprises diethyl ether, di-n-propyl ether, isopropyl ether, anisole, ethoxybenzene, propoxybenzene, butoxybenzene, 2-methoxytoluene, 3-methoxytoluene, 4-methoxytoluene, benzyl ethyl ether, diphenyl ether, dibenzyl ether, tetrahydrofuran, 2,3-dihydropyran, tetrahydropyran, 2-methyl tetrahydropyran, benzene, toluene, xylene, ethylbenzene, diethylbenzene or cyclohexylbenzene.

Representative examples of the invention are described as the following paragraphs.

General Procedure for Preparing the Compound Having a Formula (1)

Isocyanates and phenolic compounds are dissolved in a non-polar solvent to form a mixture. Preferably, the mixture is a homogenous mixture. Heat the mixture to 60~100° C. for performing reaction of the isocyanates and phenolic compounds. Some catalysts, such as organic tin compound, organic zinc compound or amines, are added into the mixture to speed up the reaction. The reaction is monitored by FTIR. When the reaction is completed, remove the non-polar solvent and then purify the product by distillation or column chromatography to obtain the compound having a formula (1).

Representative Example of the Compound Having a Formula (1): (4-(2-(4-Hydroxyphenyl)Propan-2-Yl)Phenyl (3-(Trimethoxysilyl)Propyl)Carbamate 3-(Triethoxysilyl)propyl isocyanate (5.0 g) and bisphenol-A (3.69 g) are dissolved in toluene (50 ml) to form a reaction mixture. Heat the reaction mixture to 80~100° C. and add an organic tin compound as a catalyst. Bisphenol A is monitored by thin layer chromatography and totally consumed after 12 hours. The crude product is purified and removed toluene. FTIR is used to monitor functional group transformation. When a peak at about 1716 $cm^{-1}$ is observed, it means a compound having carbamate group is produced. Finally, (4-(2-(4-hydroxyphenyl)propan-2-yl) phenyl (3-(trimethoxysilyl)propyl)carbamate (7.8 g) is obtained and further identified by FTIR and $^1$H-NMR.

FTIR(KBr):1716 $cm^{-1}$, 3350 $cm^{-1}$ (NH, urethane), 950 $cm^{-1}$ (Si—O); $^1$H-NMR (400 MHz, d-DMSO): δ(ppm)=0.5 (t, 6H), 1.2 (t, 27H), 1.5 (t, 18H), 3.0 (m, 6H), 3.8 (m, 18H), 6.7 (m, 6H), 7.0 (m, 12H), 7.2 (m, 6H), 7.7 (t, 3H), 9.2 (s, 3H).

The isocyanates used in the general procedure for preparing the compound having a formula (1) further comprises hexyl isocyanate, octyl isocyanate, dodecyl isocyanate, octadecyl isocyanate, cyclohexyl isocyanate, trimethylsilyl isocyanate, 3-(triethoxysilyl)propyl isocyanate, 3-(trimethoxysilyl)propyl isocyanate, phenylethyl isocyanate, methyl isocyanate, ethyl isocyanate, propyl isocyanate, eicosyl isocyanate or tetracosyl isocyanate.

The phenolic compounds used in the general procedure for preparing the compound having a formula (1) further comprises 2,2-bis(4-hydroxyphenyl) methane (bisphenol F), the compound having a formula (2), the compound having a formula (3) or the compound having a formula (4) that described in the aforementioned embodiments.

General Procedure for Preparing the Inorganic Bead

The compound having a formula(1) condensates with a hydroxy group, an amino group or a thiol group on surface of the inorganic particle in a medium, so as to modify the surface of the inorganic particle. After condensation reaction, the compound having a formula(1) has bond on the surface of the inorganic particle to form the inorganic bead. Isolate the inorganic bead from the medium by filtration and then dry it, finally, the inorganic bead is obtained. The inorganic bead is a surface-functionalized inorganic particle.

General Procedure for Preparing the Organic-Inorganic Hybrid Material

Provide the compound having a formula (1), or the product prepared from the isocyanates and phenolic compound, or diphenyl carbonate, or the inorganic bead. In particular, the compound having a formula (1), or the product prepared from the isocyanates and phenolic compound has a carbamate group in their structure, so as to possess very good compatibility with a polymer or prepolymer that has carbonyl group. Add the compound having a formula (1), or the product prepared from the isocyanates and phenolic compound, or diphenyl carbonate, or the inorganic bead into a prepolymer that comprises polyurethane prepolymer, epoxy oligomer or a precursor of polyimide "polyamic acid" to form a mixture, and use FTIR to analyze the mixture. The FTIR analysis shows a peak at 950 $cm^{-1}$ position (Si—O—R). Dilute the mixture with a solvent and then add 0.1~5 wt % of acid catalyst, such as HCl, $HNO_3$ or HOAc to form a reaction composition. Place the reaction composition into an oven at 60° C. for performing sol gel reaction. After 24~48 hours, the peak at 950 $cm^{-1}$ position disappears and the sol gel reaction is completed. At the same time, a new peak at 1000~1100 $cm^{-1}$ position (Si—O—Si) in FTIR is observed. After removing the solvent and purification, the invented organic-inorganic hybrid material is obtained.

General Procedure for Preparing the PU Prepolymer

The polyurethane (PU) prepolymer is prepared by polycondensation of the isocyanates and polyols. The isocyanates comprise IPDI or HDI and the polyols comprises PEG, PTMEG, PCL or PCPO. The polycondensation is performed at 60-80° C. Solvents including DMF, NMP, THF, DMSO or anisole are added for increasing the reaction rate. After the polycondensation is finished, a characteristic peak of carbamate group is observed in the FTIR spectrum.

The PU prepolymers and the compound having a formula (1) ((4-(2-(4-hydroxyphenyl)propan-2-yl)phenyl (3-(trimethoxysilyl)propyl)carbamate) are used to prepare the invented organic-inorganic hybrid material according to the general procedure described in paragraph [0098][0099], respectively. The experimental results are list in TABLE 1. CA represents water contact angle and silica (%) represents the weight percentage of the inorganic compounds in the invented organic-inorganic hybrid material. The value after polyols represents their molecular weight, for example, PTMEG 2000 is a PTMEG has molecular weight of 2,000 g/mol.

TABLE 1

| Experiment | Compositions (gram) | | | Water | | |
| --- | --- | --- | --- | --- | --- | --- |
| | Isocyanate (mol) | Polyol (mol) | Silica (%)$^)$ (wt %) | $CA^)$ (°) | adsorption (wt %) | Film quality |
| No. 1 | MDI(1.05) | PCL2000(4.2) | 0 | — | — | X |
| No. 2 | MDI(1.05) | PCL2000(4.2) | 4.4 | 81.1 | 8.6 | ○ |
| No. 3 | MDI(1.05) | PCPO2000(4.2) | 0 | — | — | X |
| No. 4 | MDI(1.05) | PCPO2000(4.2) | 4.4 | 82.3 | 3.8 | ⊚ |
| No. 5 | MDI(1.05) | PTMEG2000(4.2) | 0 | — | — | X |
| No. 6 | MDI(1.05) | PTMEG2000(4.2) | 4.4 | 79.1 | gelation | X |
| No. 7 | MDI(1.05) | PTMEG2000(4.2) | 13.0 | 83.2 | 10.7 | ⊚ |
| No. 8 | MDI(1.05) | PTMEG2000(4.2) | 26.0 | 85.0 | 7.3 | ⊚ |
| No. 9 | MDI(1.05) | PTMEG2000(4.2) | 36.0 | 86.6 | 5.6 | ⊚ |
| No. 10 | MDI(1.05) | PTMEG2000(4.2) | 49.0 | 85.7 | 4.2 | ⊚ |

X represents poor film quality;
○ represents good film quality;
⊚ represents excellent film quality Experiment No. 1, No. 3 and No. 5 are control group and not added the compound having a formula (1), respectively. As shown FIG. 1, the FTIR spectrum show a peak at 1737 cm$^{-1}$ which is a carbamate group formed by MDI and PCL 2000.

Figure 2:
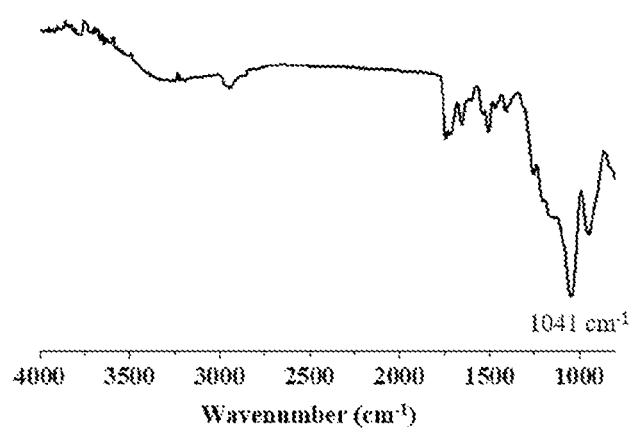
FIG. 2 is a FTIR spectrum directed to the product prepared in experiment No. 2.

Experiment No. 2 is to add the compound having a formula(1) into the PU prepolymer prepared from MDI and PCL 2000 to form a mixture, dilute the mixture with a proper solvent and add 0.1~5 wt. % of acid catalyst. Allow the film formation in an oven at 60° C. The sol-gel reaction is finished after 24~48 hours, remove the solvent and use FTIR to monitor the functional group transformation. The peak at 950 cm$^{-1}$ (Si—O—R) disappears and a new peak at 1041 cm$^{-1}$ (Si—O—Si) is observed. After purification and drying, the organic-inorganic hybrid material prepared from the PU prepolymer and the compound having a formula (1) is obtained and the FTIR spectrum is shown in FIG. 2.

Figure 3:
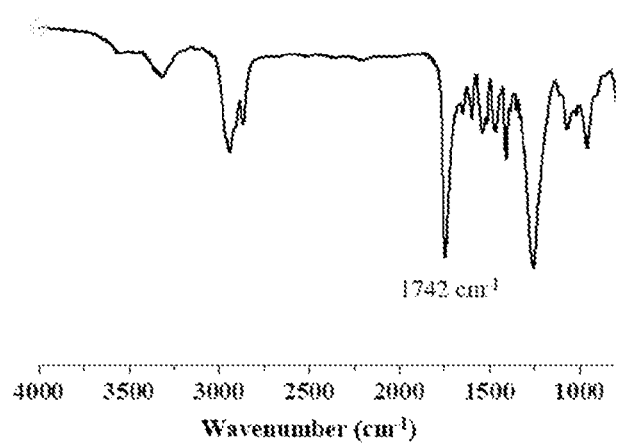
FIG. 3 is a FTIR spectrum directed to the product prepared in experiment No. 3.
Figure 4:
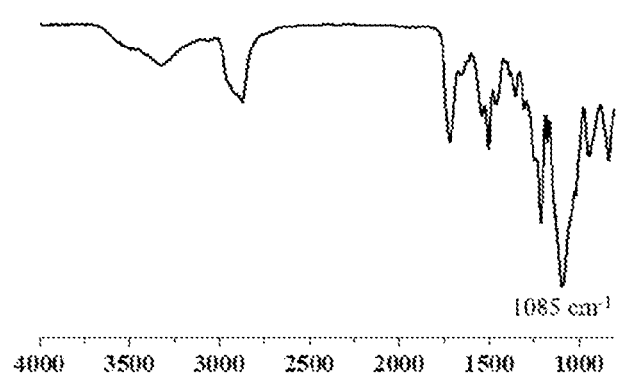
FIG. 4 is a FTIR spectrum directed to the product prepared in experiment No. 4.

The FTIR spectrum of experiment No. 3 is shown in FIG. 3. A peak at 1742 cm$^{-1}$ is observed and it means carbamate functional group. In comparison with experiment No. 4, the experiment No. 4 is the organic-inorganic hybrid material prepared from the PU prepolymer formed by polycondensation of MDI and PCPO2000 and the compound having a formula (1). The FTIR spectrum as shown in FIG. 4, a peak at 1085 cm$^{-1}$ (Si—O—Si) is observed.

Figure 5:
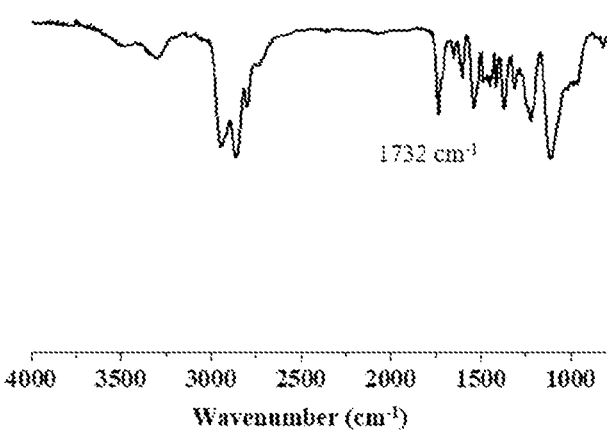
FIG. 5 is a FTIR spectrum directed to the product prepared in experiment No. 5.
Figure 6:
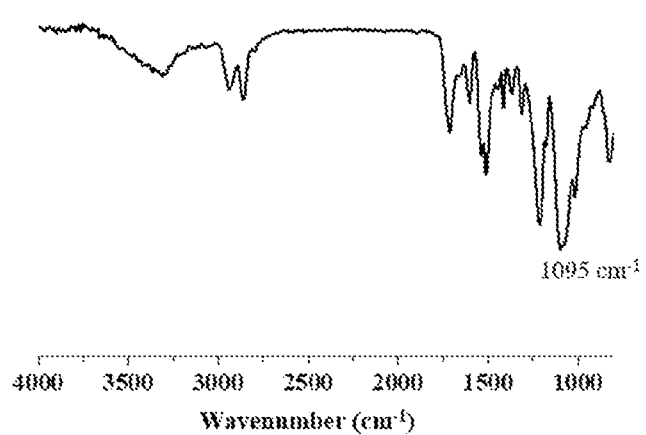
FIG. 6 is a FTIR spectrum directed to the product prepared in experiment No. 10.

The FTIR spectrum of experiment No. 5 is shown in FIG. 5. A peak at 1732 cm$^{-1}$ is observed. In comparison with experiment No. 5, experiment No. 10 is add the inorganic bead containing silica and having a size of 20~1,000 nm to the prepolymer formed by polycondensation of MDI and PTMEG2000 to form a mixture, dilute the mixture with a proper solvent and add 0.1~5 wt. % of acid catalyst. Allow the film formation in an oven at 60° C. The sol-gel reaction is finished after 24~48 hours, remove the solvent and use FTIR to monitor the functional group transformation. The peak at 950 cm$^{-1}$ (Si—O—R) disappears and a new peak at 1095 cm$^{-1}$ (Si—O—Si) is observed. After purification and drying, the organic-inorganic hybrid material prepared from the PU prepolymer and the inorganic bead is obtained. The FTIR spectrum is shown in FIG. 6.

According to the aforementioned experimental results, the compound having a formula(1) or its modified inorganic bead effectively enhance the properties of the organic-inorganic hybrid material, such as waterproof property and film quality. The organic-inorganic hybrid material has water contact angle more than 80 degree and 5~50% of the inorganic compounds. As a result, the organic-inorganic hybrid material is good to construct waterproof devices or insulator.

Representative Example of the Isocyanates Prepared from the Carbonate Containing Compounds (3-aminopropyl)trimethoxysilane (7.19 g) and polycarbonate (10.0 g) are mixed in a solvent to form a reaction mixture. The solvent comprises diethyl ether, di-n-propyl ether, isopropyl ether, anisole, ethoxybenzene, propoxybenzene, butoxybenzene, 2-methoxytoluene, 3-methoxytoluene, 4-methoxytoluene, benzyl ethyl ether, diphenyl ether, dibenzyl ether, tetrahydrofuran, 2,3-dihydropyran, tetrahydropyran, 2-methyl tetrahydropyran, benzene, toluene, xylene, ethylbenzene, diethylbenzene or cyclohexylbenzene. Firstly, heat the reaction mixture to 80~90° C. and keep temperature for 1 hour at least, and then raise the temperature to 200~250° C. for the second heating stage. The second heating stage is operated under vacuum, and pressure is 0.0001-400 mmHg. Finally, a isocyanate derived from (3-aminopropyl)trimethoxysilane (5.12 g) is obtained.

The isocyanate derived from (3-aminopropyl)trimethoxysilane has a characteristic peak at 2260 cm$^{-1}$ in FTIR spectrum.

The amino compound used in the aforementioned representative example of isocyanates further comprises benzylamine, ethylamine, phenethylamine, propylamine, 3-phenylpropylamine, butylamine, 4-phenylbutylamine, pentylamine, 5-phenylpentylamine, hexylamine, 6-phenylhexylamine, isobutylamine, aminoethylpiperazine, 1-methylpiperazine, 3-morpholinopropylamine, aminoethylpiperazine or (3-Aminopropyl)triethoxysilane.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A product produced from a sol-gel reaction of a composition, wherein the product is an organic-inorganic hybrid material comprising 5-50 wt % of inorganic compounds, based on total weight of the product, and a structure having a characteristic peak at 1050±50 cm$^{-1}$ in FTIR spectrum; wherein the composition comprises a prepolymer and an inorganic bead; wherein the inorganic bead is an inorganic particulate material of inorganic particles that have been surface functionalized with a compound having a formula (1):

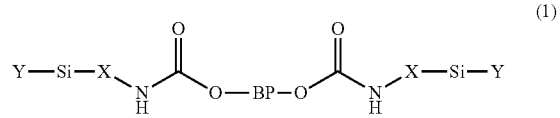

(1)

where BP represents a polyphenol or a halogenated polyphenol;

X is (—CH$_2$—)m or O, and m is a integer of 1 to 10;

Y is (H)$_a$, (—OH)$_b$, (—OCH$_3$)$_c$, (—OCH$_2$CH$_3$)$_d$ or (—OCH$_2$CH$_2$CH$_3$)$_e$, where the sum of a, b, c, d, and e is equal to 3; and a, b, c, d, and e are each a number of 0 to 3, provided that at least one of c, d, and e is a number of 1 to 3.

2. The product produced from a sol-gel reaction of a composition according to claim 1, wherein the compound having a formula (1) is 4-(2-(4-hydroxyphenyl)propan-2-yl)phenyl(3-(trimethoxysilyl)propyl)carbamate.

3. The product produced from a sol-gel reaction of a composition according to claim 1, wherein the inorganic particulate material comprises inorganic particles of silicon oxide, silicon sulfide, aluminum oxide, aluminum sulfide, titanium oxide, titanium sulfide, germanium oxide, germanium sulfide, iron oxide, iron sulfide, barium oxide, barium sulfide, zinc oxide, zinc sulfide, copper oxide, copper sulfide, chromium oxide, chromium sulfide, niobium oxide, niobium sulfide, manganese oxide, manganese sulfide, tin oxide, tin sulfide, lithium oxide, lithium sulfide, cerium oxide, cerium sulfide, cobalt oxide, cobalt sulfide, SiO$_2$, TiO$_2$, ZnO, ZrO$_2$, Fe$_2$O$_3$, BaTiO$_3$, LiNbO$_3$, CdSe, CuO, BaZrO$_3$, Cr$_2$O$_3$, Nb$_2$O$_5$, CsO$_2$, FeTiO$_3$d , FeS, mixture of Al$_2$O$_3$ and TiO$_2$, mixture of Al$_2$O$_3$ and ZrO$_2$, MnO$_2$, SnO or ZnS.

4. The product produced from a sol-gel reaction of a composition according to claim 1, wherein the inorganic particulate material of inorganic particles has average diameters between 20 to 1,000 nm.

5. The product produced from a sol-gel reaction of a composition according to claim 1, wherein the prepolymer comprises a polyurethane prepolymer, an epoxy oligomer or a polyamic acid.

6. The product produced from a sol-gel reaction of a composition according to claim 1, wherein the prepolymer has molecular weight between 5,000 and 50,000 Da.

7. A process for preparation of a product comprising:
(1) providing an inorganic bead; wherein the inorganic bead is an inorganic particulate material of inorganic particles that have been surface functionalized with a compound having a formula (1)

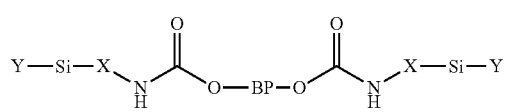

(1)

where BP represents a polyphenol or a halogenated polyphenol;

X is $(-CH_2-)_m$ or O, and m is a integer of 1 to 10;

Y is $(H)_a$, $(-OH)_b$, $(-OCH_3)_c$, $(-OCH_2CH_3)_d$ or $(-OCH_2CH_2CH_3)_e$, and where the sum of a, b, c, d, and e is equal to 3; and a, b, c, d, and e are each a number of 0 to 3, provided that at least one of c, d, and e is a number of 1 to 3;

(2) adding the inorganic bead to a prepolymer having molecular weight between 5,000 and 50,000 Da to form a mixture, wherein the mixture comprises 10-60 wt % of the prepolymer, based on total weight of the mixture; and (3) performing a sol-gel reaction of mixture to produce the product; wherein the product is an organic-inorganic hybrid material comprising 5-50 wt % of inorganic compounds, based on total weight of the product, and a structure having a characteristic peak at 1050±50 $cm^{-1}$ in FTIR spectrum.

8. The process according to claim 7, wherein the compound having a formula (1) is 4-(2-(4-hydroxyphenyl)propan-2-yl)phenyl(3-(trimethoxysilyl)propyl)carbamate.

9. The process according to claim 7, wherein the inorganic particulate material comprises inorganic particles of silicon oxide, silicon sulfide, aluminum oxide, aluminum sulfide, titanium oxide, titanium sulfide, germanium oxide, germanium sulfide, iron oxide, iron sulfide, barium oxide, barium sulfide, zinc oxide, zinc sulfide, copper oxide, copper sulfide, chromium oxide, chromium sulfide, niobium oxide, niobium sulfide, manganese oxide, manganese sulfide, tin oxide, tin sulfide, lithium oxide, lithium sulfide, cerium oxide, cerium sulfide, cobalt oxide, cobalt sulfide, $SiO_2$, $TiO_2$, $ZnO$, $ZrO_2$, $Fe_2O_3$, $BaTiO_3$, $LiNbO_3$, $CdSe$, $CuO$, $BaZrO_3$, $Cr_2O_3$, $Nb_2O_5$, $CsO_2$, $FeTiO_3$, $FeS$, mixture of $Al_2O_3$ and $TiO_2$, mixture of $Al_2O_3$ and $ZrO_2$, $MnO_2$, $SnO$ or $ZnS$.

10. The process according to claim 7, wherein the inorganic particulate material of inorganic particles has an average diameter between 20 and 1,000 nm.

11. The process according to claim 7, wherein the prepolymer comprises a polyurethane prepolymer, an epoxy oligomer or a polyamic acid.

12. The process according to claim 7, wherein the mixture further comprises a solvent, an additive or its combination.

13. The process according to claim 12, wherein the solvent comprises tetrahydrofuran, dimethyl sulfoxide, dimethylformamide, N-methyl-2-pyrrolidone or anisole.

14. The process according to claim 12, wherein the additive comprises boric acid, phosphoric acid, hydrochloride acid, sulfuric acid, nitric acid, acetic acid, formic acid, propionic acid, alkali metal hydroxide, sodium phosphate, aliphatic amine, piperidine and its derivatives, imidazole and its derivatives or nitrogen heterocyclic compounds.

15. The process according to claim 7, wherein the sol-gel reaction is performed at a temperature between 20 and 60° C.

* * * * *